United States Patent [19]
Keith

[11] Patent Number: 4,542,013
[45] Date of Patent: Sep. 17, 1985

[54] TRINITROGLYCEROL SUSTAINED RELEASE VEHICLES AND PREPARATION THEREFROM

[75] Inventor: Alec D. Keith, Miami, Fla.

[73] Assignee: Key Pharmaceuticals, Inc., Miami, Fla.

[21] Appl. No.: 523,988

[22] Filed: Aug. 16, 1983

Related U.S. Application Data

[63] Continuation-in-part of Ser. No. 281,389, Jul. 8, 1981, abandoned.

[51] Int. Cl.4 .................... A61K 31/21; A61K 31/79; A61K 31/74; A61L 15/03
[52] U.S. Cl. ........................................ 424/28; 424/22; 424/80; 514/509
[58] Field of Search ..................... 424/22, 28, 80, 298

[56] References Cited

U.S. PATENT DOCUMENTS 4,291,015 9/1981 Keith et al. ............................ 424/28

Primary Examiner—Shep K. Rose
Attorney, Agent, or Firm—Wegner & Bretschneider

[57] ABSTRACT

A trinitroglycerol-containing substantially disaccharide-free polymeric diffusion matrix is provided for the transdermal systemic delivery of trinitroglycerol through the skin of a patient. The polymeric diffusion matrix contains sufficient trinitroglycerol to be released over a prolonged period of time and comprises a first lower molecular weight, partially hydrolyzed polyvinylalcohol component, a second higher molecular weight, essentially fully hydrolyzed polyvinylalcohol component, and glycerol.

8 Claims, 2 Drawing Figures

TRINITROGLYCEROL SUSTAINED RELEASE VEHICLES AND PREPARATION THEREFROM

CROSS REFERENCE TO RELATED APPLICATION

This application is a continuation-in-part of U.S. patent application Ser. No. 281,389, filed July 8, 1981, now abandoned.

BACKGROUND OF THE INVENTION

The invention provides an improved transdermal diffusion matrix for the sustained release of trinitroglycerol. The anti-anginal activity of trinitroglycerol has been well-known for many years. A sustained release of trinitroglycerol through the skin for systemic activity has been known for several decades; see Davis et al, Am. J. Med. Sci., 259-263 (September 1955). Moreover, NITROL (Kremers-Urban) and NITRO-BID (Marion) have been on the market for some time. Gross et al, *Archiv für Toxikologie*, Vol. 18, 194-199, 331-334 (1960), noted the sustained release of trinitroglycerol in studies that confirm that trinitroglycerol is delivered through the skin at a steady rate. The rate-determining step for trinitroglycerol systems is controlled by the skin itself. Around 1970, various sustained release forms were proposed as exemplified by Zaffaroni, U.S. Pat. No. 3,942,751, although none of the embodiments disclosed was put into use. Recently, NITRO-DUR (Key Pharmaceuticals, Inc., Miami, Fla.; Keith et al., U.S. Pat. No. 4,291,015) was commercially introduced and favorably received. Two other dissimilar products for the same use have also been proposed for commercial introduction (Searle; Ciba).

SUMMARY OF THE INVENTION

In accordance with a first aspect of the invention there is provided a substantially disaccharide-free polymeric diffusion matrix for the transdermal systemic delivery of trinitroglycerol through the skin of a patient, said polymeric diffusion matrix containing sufficient trinitroglycerol to be released over a prolonged period of time and which comprises a first lower molecular weight water-soluble polymer with hydration sites, a second higher molecular weight water-soluble polymer with hydration sites, and glycerol. In a preferred embodiment, the polymeric diffusion matrix comprises from about 10 to about 40% lower molecular weight, partially hydrolyzed polyvinylalcohol component as the lower molecular weight water-soluble polymer, from about 2 to about 15% higher molecular weight polyvinylalcohol component as the higher molecular weight water-soluble polymer, and from about 2 to about 25% glycerol. The lower molecular weight polyvinylalcohol component has a molecular weight of from about 5,000 to about 40,000. The higher molecular weight polyvinylalcohol component has a molecular weight of from about 90,000 to about 150,000 and is essentially completely hydrolyzed.

The lower molecular weight polyvinylalcohol component as used herein is always a partially hydrolyzed form with a degree of hydrolysis of about 75 to about 92%, preferably between about 86 and about 90%. As used in all examples herein, the degree of hydrolysis is 88%. The higher molecular weight polyvinylalcohol component generally has at least about 95% hydrolysis and preferably at least about 98% hydrolysis. When used in the examples, the degree of hydrolysis is about 98 to 99%.

In a further embodiment, the substantially disaccharide-free matrix includes polyvinylpyrrolidone in an amount up to about 2% by weight having a molecular weight of from about 20,000 to about 60,000.

The matrix may also include an alkanolamide present in an amount up to 5% by weight and preferably from about 0.1 to about 3% by weight.

In accordance with a second aspect of the invention there is provided a flowable gel preparation suitable for transdermal application to a patient to deliver trinitroglycerol over a prolonged period of time. The flowable gel is based upon a polymer capable of binding trinitroglycerol and capable of releasing trinitroglycerol though the skin of the patient.

In yet another aspect of this invention, a buccal or sublingual dosage form is provided.

BRIEF DESCRIPTION OF THE DRAWINGS

FIG. I is a cross-sectional view of a polymeric diffusion matrix bandage which permits the direct adherence of the matrix to the skin of the patient, eliminating the need for adhesive tapes.

FIG. II is a cross-sectional view of an adhesive tape bandage which comprises a barrier baseplate, matrix anchor, the drug matrix, and a barrier coverstrip attached to the facestock/adhesive tape.

DETAILED DESCRIPTION OF THE INVENTION

Figure 1:
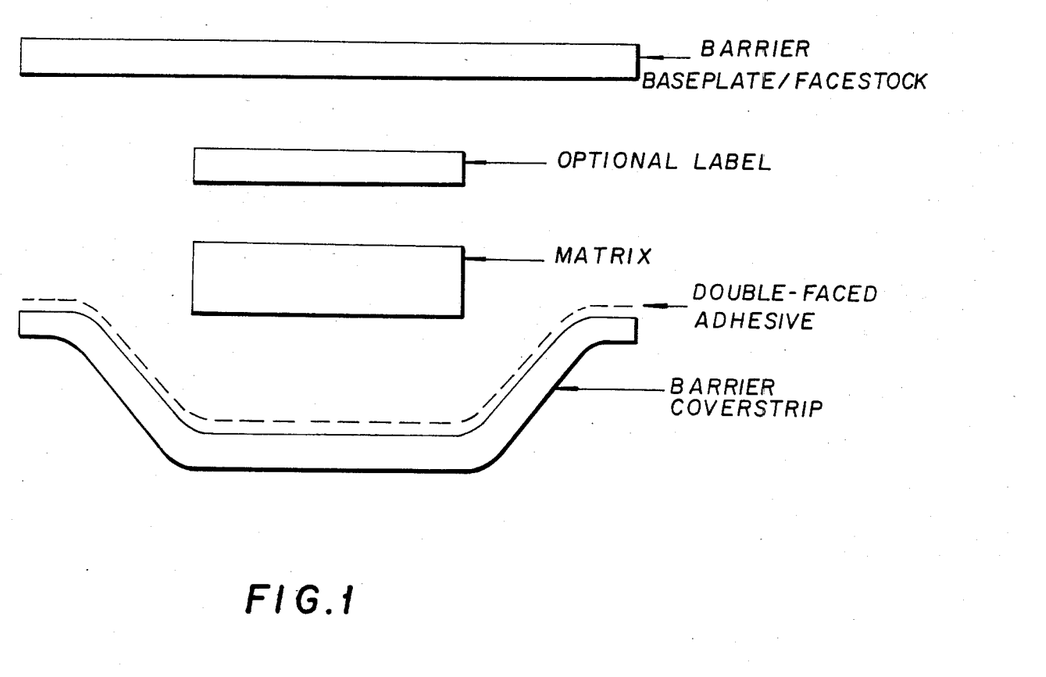
Figure 2:
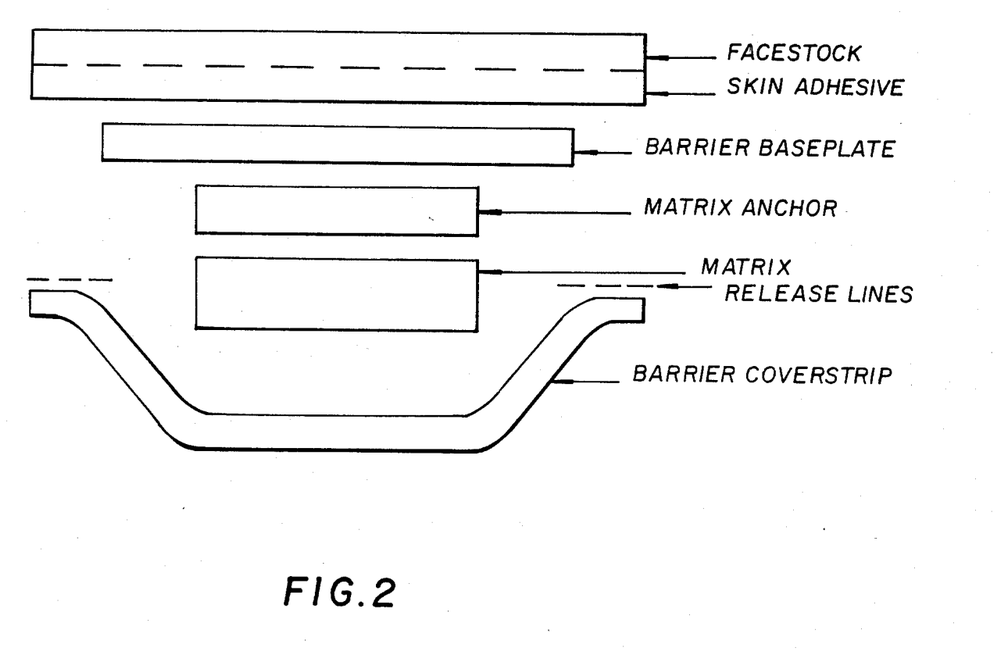

The invention provides alternative forms for the sustained release of trinitroglycerol that do not require the presence of lactose, a disaccharide. Up to the present time, lactose has generally been included in trinitroglycerol preparations because lactose triturate is the form in which trinitroglycerol has generally been available to the pharmaceutical industry. (It should be recognized that trinitroglycerol in concentrated form is highly explosive, which is the reason for a general requirement heretofore of the lactose triturate form.)

NITRO-DUR is a sustained release preparation that has been favorably commercially received. The polymeric diffusion matrix in accordance with the present invention is superior to NITRO-DUR in terms of being less "wet" which, quite apart from the subjective perspective of a wearer, contributes to minimizing the debonding of the adhesive, thus permitting a prolonged wearing. The improved matrix promotes the intimate adherence throughout this prolonged wearing period of the polymeric diffusion matrix on the skin, intimate diffusional contact being desired for the sustained release of the drug to the patient.

In a first aspect of this invention, a disaccharide-free polymeric diffusion matrix is provided. The polymeric diffusion matrix is suitable for systemic trinitroglycerol delivery through the skin of a patient. In a preferred embodiment, the trinitroglycerol is added as a trinitroglycerol/solvent solution. The solvents used include polyethylene glycol, dipropylene glycol, acetin, diacetin, and acetone. The amount of solvent ranges from about 5% to about 20%.

The matrix comprises from about 10 to about 40% lower molecular weight water-soluble polymer, for example polyvinylalcohol, and preferably from about 25 to about 30% by weight; from about 2 to about 15% molecular weight of the higher molecular weight water-soluble polymer, and preferably about 3%; and from about 2 to about 25% glycerol, preferably from about 10 to about 15% by weight. The molecular weight of the lower molecular weight polyvinylalcohol is from about 5,000 to about 40,000, preferably from about 20,000 to about 23,000. The molecular weight of the higher molecular weight water-soluble polymer component is from about 90,000 to about 150,000, and preferably about 115,000.

In a further embodiment, the polymeric diffusion matrix includes polyvinylpyrrolidone in an amount up to about 2% by weight having a molecular weight from about 20,000 to about 60,000.

The matrix of the invention also includes a surface active agent such as an alkanolamide in an amount up to about 5%, preferably 0.1 to about 3% by weight. These surface active agents are $C_8$–$C_{18}$ alkanolamides, for example, lauric myristic, lauric, myristic, isostearic, capric, and linoleic alkanol amides and combinations thereof. The alkanolamide can be, for example, Monamid 716 (Mona), Monamid 716P (Mona), Monateric LMAB (Mona), or Monaquat PTL (Mona). The above agents all possess properties desired in surface active agents.

A lactose-free triturate is provided in a second aspect of the invention, which is suitable as a means for providing trinitroglycerol when it is not desired to have lactose in the preparation. It is to be understood that mixtures of the novel triturate without lactose may be used in combination with lactose triturate when desired for a particular use, the exemplifications of the invention which follow showing only the lactose-free formulations.

Trinitroglycerol in a stable form is provided by binding the trinitroglycerol to a polymeric substance which preferably is a lower molecular weight water-soluble polymer, polyvinylpyrrolidone, or a mixture of these polymers. With a lower molecular weight polyvinylalcohol of from about 2,000 to about 15,000 molecular weight, and still more preferably of about 10,000 molecular weight, a solvent solution of the trinitroglycerol may be poured into the polyvinylalcohol to obtain the triturate without heating. Typically, the trinitroglycerol is leached from lactose triturate with a solvent and the solvent containing the trinitroglycerol is poured into the polyvinylalcohol, the solvent subsequently being evaporated to yield the desired trinitroglycerol bound to the polyvinylalcohol. A similar preparation of trinitroglycerol may be made with other polymers such as polyvinylpyrrolidone having a molecular weight of from about 20,000 to about 90,000. The amount of trinitroglycerol is not critical, provided that phase separation is avoided (which phase separation would lead to the risk of a dangerous explosion). Up to 20% trinitroglycerol has been experimentally introduced into a polyvinylalcohol preparation, although more generally a 10% trinitroglycerol preparation has been produced.

It should also be noted that it is expected that, when commercial demand for the polymeric triturate is sufficient, the preparation of the polymeric triturates of the present invention, while initially produced by the method described above from lactose triturate, will be replaced by procedures that will directly bind the trinitroglycerol to the polymeric substances without an intermediate lactose triturate step.

It is to be understood that other triturates may be formed. It is, of course, essential and very important from the standpoint of safety that sufficiently low concentrations of trinitroglycerol be present to be certain to avoid phase sepration. It is to be understood that as a practical matter a maximum of about 20% (and usually only about 10%) trinitroglycerol is included in any of the triturates of the present invention. Examples of triturates in the explosives field with higher percentages of nitroglycerin are found in Berthmann et al, British Patent Specification No. 1,090,184, which discloses methods for the manufacture of various triturates. It is to be understood that any pharmacologically acceptable triturate may be prepared, including triturates of the same polymers of Berthmann et al, but with a much lower concentration of trinitroglycerol than the explosive levels of the composition of that patent. As such polymers may be mentioned polymethacrylate, polyvinyl acetate, ethyl acrylate-vinyl chloride copolymer ("ASTRALON"), and polymethyl methacrylate.

It should be noted that a difference exists between the polymeric forms of trinitroglycerol of the invention and lactose triturate so that the two substances cannot be used completely interchangeably. The polymeric forms of the invention appear to provide products of superior mechanical properties as compared to products based upon lactose.

When applied to the skin as a flowable gel preparation, ethanol or isopropyl alcohol is advantageously incorporated into the product, up to about 30% of ethanol or isopropyl alcohol being preferred, and in a still more preferred embodiment about 20% is utilized. Isopropyl myristate is a further preferred ingredient, with an amount of up to about 5% incorporated into the final product. (All percentages are by weight in this description unless indicated to the contrary.) The flowable gel may be directly applied to the skin of a patient through conventional means used for more traditional forms, e.g., by spreading the flowable gel from a tube onto a Saran sheet that is then placed over the skin. In a more preferred embodiment, a bandage with a concave portion is provided; typically the flowable gel is squeezed from a toothpaste-type of tube into the concavity. This bandage, which advantageously has an annular adhesive ring around the concavity, is placed onto the skin and held in place with the bandage adhesive ring.

The flowable gel preparation of one aspect of the invention is prepared by mixing an appropriate amount of polymeric trinitroglycerol of the invention with, for example, isopropyl alcohol and isopropyl myristate.

A further embodiment of the invention contemplates a fixed dimension gel which in terms of its shape and self-supporting characteristics is provided as an alternative to the diffusion matrix described in the above-mentioned patent to Keith et al. In the preparation of the preferred fixed dimension gel having a mixture of polyvinylalcohol and polyvinylpyrrolidone, two stock solutions are prepared, one of polyvinylpyrrolidone and one of polyvinylalcohol. In the polyvinylpyrrolidone stock solution there is added isopropyl alcohol and any isopropyl myristate, and optionally sodium borate. In the second stock solution based upon polyvinylalcohol which is bound to trinitroglycerol there is added water and some of the isopropanol. The two stock solutions are then mixed with stirring to yield the fixed dimension gel of the invention.

It should also be noted that in the embodiments that refer to a triturate or to a polymeric mixture of polymerically-bound trinitroglycerol, varying percentages of trinitroglycerol may be used. Unless otherwise specified, however, when no fixed percentage of trinitroglycerol has been mentioned, the amount is 10% of the particular polymer. As noted elsewhere, higher amounts have been prepared, including 20%, and are contemplated within the scope of this invention. (It again is to be cautioned that working with very high percentages of trinitroglycerol increases the dange of phase separation, which is to be avoided in any event due to the risk of explosion. Great caution is to be exercised by the reader when deviation is made from examples in a manner to increase percentages of trinitroglycerol that would bring about phase separation.)

It is to be noted that a bandage backing is desirable for the polymeric diffusion matrix of the invention to provide diffusional contact with the skin. In a preferred embodiment, the polymeric diffusion matrix is affixed to a patient in the form of a bandage depicted in FIG. I. This form provides direct adherence of the matrix to the skin of the patient. The barrier layer, a combination baseplate and facestock, comprises an inert backing material including metal foils and polyesters. The drug-containing matrix, in its liquid state, is cast between the above-described barrier layer and a coverstrip layer with a double-faced adhesive. The barrier coverstrip includes inert materials such as metal foils and polyesters. A label may optionally be included for the rapid identification of drug and dose in emergency situations.

In a further embodiment, as depicted by FIG. II, the bandage includes a facestock layer with skin adhesive which comprises a foam, film-type, non-woven, or vinyl tape with an acrylic, silicone, or rubber adhesive. Useful backings include, for example, Mylar (polyethylene terephthalate, du Pont), polyethylene, and a variety of polyesters. Also included is a barrier baseplate of inert backing material such as metal foil or polyester film. It is to be noted that the bandage should contain at least one polyester or foil layer on both sides of the matrix to prevent evaporation. As previously noted, the liquid matrix is cast between barrier layers. A matrix anchor between the barrier baseplate and polymeric diffusion matrix comprises a synthetic or non-woven material layer, such as nylon or polyester film. Prior to administration the outermost layer, i.e. the barrier coverstrip, is pulled away and the matrix in bandage form is affixed to the patient.

As a further embodiment in the packaging of the present matrix, the backing layer may be a conventional backing layer such as is disclosed in Keith et al. U.S. Pat. No. 4,291,015, particularly where the polymeric diffusion matrix is supported through an annular adhesive strip surrounding the polymeric diffusion matrix. The drug-containing diffusion matrix is placed in a cavity provided in an inert backing material. Useful backing materials include metal foils such as aluminum foil, polyolefins such as polyethylene and polypropylene, polyesters such as polyethylene terephthalate, polyamides such as nylon, and the like. The drug-containing diffusion matrix can be poured in its molten state into the cavity and permitted to cool. An adhesive layer is provided on the backing material surrounding the cavity. To prevent evaporative loss in the surface of the matrix, the adhesive layer and the matrix are sealed with a release layer. To use the device, the patient peels off the release layer and places the device in intimate contact with his skin. The exposed adhesive layer secures the device to the patient. A concentration gradient existing normal to the surface of the matrix and the patient's skin facilitates diffusion of the drug through the matrix into the patient's body. Thus, there is provided a device whereby a drug is delivered transdermally to a patient at a steady rate over a prolonged period of time. To apply the drug to the patient, the cover layer is peeled off. The exposed matrix is then taped onto a suitable portion of the patient's body.

A further embodiment of the invention is to utilize the fixed dimension gel, but without isopropyl alcohol or isopropyl myristate, as a buccal adminitration form. Conventional dental adhesive to maintain buccal contact may be incorporated as may a conventional backing to avoid the release of trinitroglycerol into the alimentary canal, the desired result being that the drug is delivered through the cheek and thence into the bloodstream.

A sublingual tablet may be produced by compressing the triturate of the invention in a manner similar to that used for the preparation of a sublingual tablet with lactose triturate.

The amounts of trinitroglycerol which are to be included in any of the dosage forms are similar to those which are used in the aforementioned Keith et al. patent which is incorporated herein by reference. Generally, a worker skilled in the art will be aware of a desired delivery dosage and include an excess over that amount for any of the sustained release forms. For the case of the sublingual tablet, which is designed to dissolve quickly (e.g., in a minute) the total desired amount is the total dosage for the sublingual tablet.

Disaccharide-free triturates that may be used to provide the trinitroglycerol for the polymeric diffusion matrix of the invention are described in the following examples:

EXAMPLE I

A 10% trinitroglycerol triturate that is lactose-free is produced by leaching trinitroglycerol from lactose triturate with ether, and permitting the ether-bearing trinitroglycerol to be added into the polyvinylalcohol (mw 10,000, 88% hydrolyzed). The ether mixture is first filtered to remove lactose before being added to the polyvinylalcohol. Sufficient ether mixture is added at room temperature so that the final weight of the trinitroglycerol plus polyvinylalcohol provides a 10% trinitroglycerol and 90% polyvinylalcohol mixture. After addition is complete, stirring of the mixture is conducted until there is total evaporation of the ether, yielding a white powder. This white powder is free-flowing and has a physical appearance similar to that of the starting polyvinylalcohol; it is soluble in water and the binding of the polyvinylalcohol to trinitroglycerol is shown by the maintenance of such property after centrifugation at 5,000 g for 30 minutes. Evaporation is advantageously conducted under a hood.

EXAMPLE II

Acetone is substituted for ether in Example I, the result being the formation of the same white powdery substance.

EXAMPLE III

Substituting polyvinylpyrrolidone (mw 40,000) for the polyvinylalcohol of Example I yields a powdery triturate which has the trinitroglycerol firmly bound to the polymer.

While the triturate form may be used for the preparation of the polymeric diffusion matrix of the invention, it is also contemplated that the trinitroglycerol may be directly added to the mixture in a solution form, bearing in mind the importance of avoidance of phase separation and the explosive consequences which may result from such separation.

EXAMPLE IV

Lactose triturate (10% trinitroglycerol) is added to sufficient acetone to put the trinitroglycerol in solution, after which the acetone solution is admixed with polyethylene glycol in an amount sufficient to yield an eventual trinitroglycerol concentration in a solution thereof of 18% (exclusive of the weight of the acetone). The lactose is then separated from the solution. The resultant solution is thereafter treated to heating under vacuum to yield the acetone-free trinitroglycerol solvent mixture that may be used for the introduction of the trinitroglycerol in a substantially disaccharide-free form to prepare the polymeric diffusion matrix of the invention.

EXAMPLE V

Lactose triturate (10% trinitroglycerol) is added to sufficient acetone to put the trinitroglycerol in solution, after which the acetone solution is admixed with dipropylene glycol in an amount sufficient to yield an eventual trinitroglycerol concentration in a solution thereof of 6% (exclusive of the weight of the acetone). The lactose is then separated from the solution. The resultant solution is thereafter treated to heating under vacuum to yield the acetone-free trinitroglycerol solvent mixture that may be used for the introduction of the trinitroglycerol in a substantially disaccharide-free form to prepare the polymeric diffusion matrix of the invention.

EXAMPLE VI

Lactose triturate (10% trinitroglycerol) is added to sufficient acetone to put the trinitroglycerol in solution, after which the acetone solution is admixed with diacetin in an amount sufficient to yield an eventual trinitroglycerol concentration in a solution thereof of 6% (exclusive of the weight of the acetone). The lactose is then separated from the solution. The resultant solution is thereafter treated to heating under vacuum to yield the acetone-free trinitroglycerol solvent mixture that may be used for the introduction of the trinitroglycerol in a substantially disaccharide-free form to prepare the polymeric diffusion matrix of the invention.

EXAMPLE VII

Lactose triturate (10% trinitroglycerol) is added to sufficient acetone to put the trinitroglycerol in solution, after which the acetone solution is admixed with acetin in an amount sufficient to yield an eventual trinitroglycerol concentration in a solution thereof of 6% (exclusive of the weight of the acetone). The lactose is then separated from the solution. The resultant solution is thereafter treated to heating under vacuum to yield the acetone-free trinitroglycerol solvent mixture that may be used for the introduction of the trinitroglycerol in a substantially disaccharide-free form to prepare the polymeric diffusion matrix of the invention.

EXAMPLE VIII

Lactose triturate (10% trinitroglycerol) is added to sufficient acetone to put the trinitroglycerol in solution, after which the acetone solution is admixed with polyethylene glycol (molecular weight 200) in an amount sufficient to yield an eventual trinitroglycerol concentration in a solution thereof of 6% (exclusive of the weight of the acetone). The lactose is then separated from the solution. The resultant solution is thereafter treated to heating under vacuum to yield the acetone-free trinitroglycerol solvent mixture that may be used for the introduction of the trinitroglycerol in a substantially disaccharide-free form to prepare the polymeric diffusion matrix of the invention.

The percentages given in the following examples express an amount by weight of the individual component in the final polymeric diffusion matrix.

EXAMPLE IX

Glycerol, at standard 96% concentration, is added to a vessel in an amount sufficient to prepare an 8 percent composition. Also added to the same vessel is sufficient Monamid 716P (Mona) to yield a final product with 5.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 26% of the final product. Water is added in an amount to be present in the total final composition as 38 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example IV is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE X

Glycerol, at standard 96% concentration, is added to a vessel in an amount sufficient to prepare a 14 percent composition. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to yield a total final composition 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example V is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XI

Glycerol, at sandard 96% concentration, is added to a vessel in an amount sufficient to prepare a 13.5 percent composition. Also added to the same vessel is sufficient Monamid 716P (Mona) to yield a final product with 0.5 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example V is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XII

Glycerol, at standard 96% concentration, is added to a vessel in an amount sufficient to prepare a 13 percent composition. Also added to the same vessel is sufficient Monamid 716P (Mona) to yield a final product with 1.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example V is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XIII

Glycerol, at standard 96% concentration, is added to a vessel in an amount sufficient to prepare a 12 percent composition. Also added to the same vessel is sufficient Monamid 716P (Mona) to yield a final product with 2.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example V is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XIV

Glycerol, at standard 96% concentration, is added to a vessel in an amount sufficient to prepare a 13 percent composition. Also added to the same vessel is sufficient Monateric LMAB (Mona) to yield a final product with 1.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example V is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XV

Glycerol, at standard 96% concentration, is added to a vessel in an amount sufficient to prepare a 12 percent composition. Also added to the same vessel is sufficient Monateric LMAB (Mona) to yield a final product with 2.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example V is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XVI

Glycerol, at standard 96% concentration, is added to a vessel in an amount sufficient to prepare a 11 percent composition. Also added to the same vessel is sufficient Monateric LMAB (Mona) to yield a final product with 3.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present in 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example V is added to the above mixture stirring and mixed well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XVII

Glycerol, at standard 96% concentration, is added to a vessel in an amount sufficient to prepare a 13 percent composition. Also added to the same vessel is sufficient Monaquat PTL (Mona) to yield a final product with 1.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example V is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol occurs.

The matrix is strong and exhibits only slight surface wetness.

EXAMPLE XVIII

Glycerol, at standard 96% concentration, is added to a vessel in an amount sufficient to prepare a 12 percent composition. Also added to the same vessel is sufficient Monaquat PTL (Mona) to yield a final product with 2.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example V is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XIX

Glycerol, at standard 96% concentration, is added to a vessel in an amount sufficient to prepare a 11 percent composition. Also added to the same vessel is sufficient Monaquat PTL (Mona) to yield a final product with 3.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoeschst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example V is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XX

Glycerol, at standard 96% concentration, is added to a vessel in an amount sufficient to prepare a 14 percent composition. A first high moleclar weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example VI is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XXI

Glycerol, as standard 96% concentration, is added to a vessel in an amount sufficient to prepare a 13 percent composition. Also added to the same vessel is sufficient Monamid 716P (Mona) to yield a final product with 1.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example VI is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XXII

Glycerol, at standard 96% concentration, is added to a vessel in an amount sufficient to prepare a 12 percent composition. Also added to the same vessel is sufficient Monamid 716P (Mona) to yield a final product with 2.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, polyvinylalcohol with a molecular weight of 20,000 (Mowiol 4-98, Hoechst) is added to be present as 28% of the final product. Water is added in an amount to present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example VI is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XXIII

Glycerol, at standard 96% concentration, is added to a vessel in an amount sufficient to prepare a 11 percent composition. Also added to the same vessel is sufficient Monamid 716P (Mona) to yield a final product with 3.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example VI is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XXIV

Glycerol, at standard 96% concentration, is added to a vessel in an amount sufficient to prepare a 12 percent composition. Also added to the same vessel is sufficient Monamid 716 (Mona) to yield a final product with 2.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example VI is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XXV

Glycerol, at standard 96% concentration, is added to a vessel in an amount sufficient to prepare a 12 percent composition. Also added to the same vessel is sufficient Monateric LMAB (Mona) to yield a final product with 2.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example VI is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XXVI

Glycerol, at standard 96% concentration, is added to a vessel in an amount sufficient to prepare a 12 percent composition. Also added to the same vessel is sufficient Monaquat PTL (Mona) to yield a final product with 2.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example VI is added to the above mixture followed by stirring and mixing well. The resultant matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XXVII

Glycerol, at standard 96% concentration, is added to a vessel in an amount sufficient to prepare a 14 percent composition. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example VII is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The maxtrix is strong and exhibits only slight surface wetness.

EXAMPLE XXVIII

Glycerol, at standard 96% concentration, is added to a vessel in an amount sufficient to prepare a 13 percent composition. Also added to the same vessel is sufficient Monateric LMAB (Mona) to yield a final product with 1.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present as the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example VII is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XXIX

Glycerol, at standard 96% concentration, is added to a vessel in an amount sufficient to prepare a 12 percent composition. Also added to the same vessel is sufficient Monateric LMAB (Mona) to yield a final product with 2.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example VII is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XXX

Glycerol, at standard 96% concentration, is added to a vessel in an amount sufficient to prepare a 11 percent composition. Also added to the same vessel is sufficient Monateric LMAB (Mona) to yield a final product with 3.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example VII is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XXXI

Glycerol, at standard 96% concentration, is added to a vessel in an amount sufficient to prepare a 12 percent composition. Also added to the same vessel is sufficient Monamid 716P (Mona) to yield a final product with 2.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example VII is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XXXII

Glycerol, at standard 96% concentration, is added to a vessel in an amount sufficient to prepare a 12 percent composition. Also added to the same vessel is sufficient Monateric LMAB (Mona) to yield a final product with 2.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example VII is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XXXIII

Glycerol, at standard 96% concentration, is added to a vessel in an amount sufficient to prepare a 12 percent composition. Also added to the same vessel is sufficient Monaquat PTL (Mona) to yield a final product with 2.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example VII is added to the above mixture followed by stirring and mixing well. The resultant liquid matrix is then cast between two sheets of a foil laminate, allowed to set, yielding the desired polymer matrix now suitable for use as a transdermal system for the sustained release of trinitroglycerol.

The matrix is strong and exhibits only slight surface wetness.

EXAMPLE XXXIV

Glycerol, at standard 96% concentration, is added to a vessel in an amount sufficient to prepare a 13 percent composition. Also added to the same vessel is sufficient Monateric LMAB (Mona) to yield a final product with 1.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example VII is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XXXV

Glycerol, at standard 96% concentration, is added to a vessel in an amount sufficient to prepare a 11 percent composition. Also added to the same vessel is sufficient Monateric LMAB (Mona) to yield a final product with 3.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example VII is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XXXVI

Glycerol, at standard 96% concentration, is added to a vessel in an amount sufficient to prepare a 13 percent composition. Also added to the same vessel is sufficient Monateric LMAB (Mona) to yield a final product with 1.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example VII is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XXXVII

Glycerol, at standard 96% concentration, is added to a vessel in an amount sufficient to prepare a 11 percent composition. Also added to the same vessel is sufficient Monaquat PTL (Mona) to yield a final product with 3.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example VII is added to the above mixture followed by stirring and mixing well. The resultant liquid mixture is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XXXVIII

Glycerol, at standard 96% concentration, is added to a vessel in an amount sufficient to prepare a 12 percent composition. Also added to the same vessel is sufficient Monamid 716P (Mona) to yield a final product with 2.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example VIII is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XXXIX

Glycerol, at standard 96% concentration, is added to a vessel in an amount sufficient to prepare a 12 percent composition. Also added to the same vessel is sufficient Monateric LMAB (Mona) to yield a final product with 2.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example VIII is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XL

Glycerol, at standard 96% concentration, is added to a vessel in an amount sufficient to prepare a 12 percent composition. Also added to the same vessel is sufficient Monateric LMAB (Mona) to yield a final product with 2.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example VIII is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XLI

Glycerol, at standard 96% concentration, is added to a vessel in an amount sufficient to prepare a 12 percent composition. Also added to the same vessel is sufficient Monaquat PTL (Mona) to yield a final product with 2.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 28% of the final product. Water is added in an amount to be present in the total final composition as 47 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example VIII is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XLII

Glycerol, at standard 96% concentration, is added to a vessel in an amount sufficient to prepare a 8 percent composition. Also added to the same vessel is sufficient Monamid 716P (Mona) to yield a final product with 2.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 26% of the final product. Water is added in an amount to be present in the total final composition as 41 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example IV is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XLIII

Glycerol, at standard 96% concentration, is added to a vessel in an amount sufficient to prepare a 8 percent composition. Also added to the same vessel is sufficient Monateric LMAB (Mona) to yield a final product with 2.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 26% of the final product. Water is added in an amount to be present in total final composition as 41 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example IV is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XLIV

Glycerol, at standard 96% concentration, is added to a vessel in an amount sufficient to prepare a 8 percent composition. Also added to the same vessel is sufficient Monaquat PTL (Mona) to yield a final product with 2.0 percent thereof. A first high molecular weight polyvinylalcohol component (mw 115,000; Elvanol 71-30, du Pont) is added to be present as 3% of the final product. The second component, a water-soluble polymer with hydration sites, polyvinylalcohol with a molecular weight of 20,000 (Mowiol 4-98, Hoechst) is added to be present as 26% of the final product. Water is added in an amount to be present in total final composition as 41 weight percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example IV is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is strong and exhibits only slight surface wetness.

EXAMPLE XLV

Glycerol, at standard 96% concentration, is added to a vessel in an amount sufficient to prepare a 10 percent composition. Also added to the same vessel is sufficient Monamid 716P (Mona) to yield a final product with 3 percent thereof. A first high molecular weight polyvinylalcohol component (mw 115,000; Elvanol 71-30, du Pont) is added to be present as 1.0% of the final product. The second component, a water-soluble polymer with hydration sites, polyvinylalcohol with a molecular weight of 20,000 (Mowiol 4-98, Hoechst) is added to be present as 27% of the final product. Polyvinylpyrrolidone of molecular weight 40,000 is added to be present in an amount of 1.5 percent. Water is added in an amount to yield a total final composition weight of 37.5 percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example IV is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is not as suitable as the preferred embodiment, since it is moderately wet and brittle.

EXAMPLE XLVI

Glycerol, at standard 96% concentration, is added to a vessel in an amount sufficient to prepare a 5 percent composition. Also added to the same vessel is sufficient Monamid 716P (Mona) to yield a final product with 3 percent thereof. A first high molecular weight polyvinylalcohol component (mw 115,000; Elvanol 71-30, du Pont) is added to be present as 0.4% of the final product. The second component, a water-soluble polymer with hydration sites, polyvinylalcohol with a molecular weight of 20,000 (Mowiol 4-98, Hoechst) is added to be present as 25% of the final product. Polyvinylpyrrolidone of molecular weight 40,000 is added to be present in an amount of 1.6 percent. Water is added in an amount to yield a total final composition weight of 45 percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example IV is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is not as suitable as the preferred embodiment, since it is brittle although only slightly damp.

EXAMPLE XLVII

Glycerol, at standard 96% concentration, is added to a vessel in an amount sufficient to prepare a 5 percent composition. Also added to the same vessel is sufficient Monamid 716P (Mona) to yield a final product with 3 percent thereof. A first high molecular weight polyvinylalcohol component (mw 115,000; Elvanol 71-30, du Pont) is added to be present as 1.0% of the final product. The second component, a water-soluble polymer with hydration sites, polyvinylalcohol with a molecular weight of 20,000 (Mowiol 4-98, Hoechst) is added to be present as 23% of the final product. Polyvinylpyrrolidone of molecular weight 40,000 is added to be present in an amount of 1.5 percent. Water is added in an amount to yield a total final composition weight of 46.5 percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example IV is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is not as suitable as the preferred embodiment, since it is brittle although only slightly damp.

EXAMPLE XLVIII

Glycerol, at standard 96% concentration, is added to a vessel in an amount sufficient to prepare a 11 percent composition. Also added to the same vessel is sufficient Monamid 716P (Mona) to yield a final product with 3 percent thereof. A first high molecular weight polyvinylalcohol component (mw 115,000; Elvanol 71-30, du Pont) is added to be present as 3.0% of the final product. The second component, a water-soluble polymer with hydration sites, polyvinylalcohol with a molecular weight of 20,000 (Mowiol 4-98, Hoechst) is added to be present as 22% of the final product. Polyvinylpyrrolidone of molecular weight 40,000 is added to be present in an amount of 4.0 percent. Water is added in an amount to yield a total final composition weight of 38 percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example IV is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is not as suitable as the preferred embodiment, since it is too wet although strong.

EXAMPLE XLIX

Glycerol, at standard 96% concentration, is added to a vessel in an amount sufficient to prepare a 7 percent composition. Also added to the same vessel is sufficient Monamid 716P (Mona) to yield a final product with 3 percent thereof. A first high molecular weight polyvinylalcohol component (mw 115,000; Elvanol 71-30, du Pont) is added to be present as 3.0% of the final product. The second component, a water-soluble polymer with hydration sites, polyvinylalcohol with a molecular weight of 20,000 (Mowiol 4-98, Hoechst) is added to be present as 22% of the final product. Polyvinylpyrrolidone of molecular weight 40,000 is added to be present in an amount of 0.5 percent. Water is added in an amount to yield a total final composition weight of 44.5 percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example IV is added to the above mixture followed by stirring and mixing well. The resultant liquid matrix is the cast between two sheets of a foil laminate, allowed to set, yielding the desired polymeric matrix now suitable for use as a transdermal system for the sustained release of trinitroglycerol.

The matrix is strong and exhibits only slight surface dampness.

EXAMPLE L

Glycerol, at standard 96% concentration, is added to a vessel in an amount sufficient to prepare a 8 percent composition. Also added to the same vessel is sufficient Monamid 716P (Mona) to yield a final product with 5 percent thereof. A first high molecular weight polyvinylalcohol component (mw 115,000; Elvanol 71-30, du Pont) is added to be present as 3.0% of the final product. The second component, a water-soluble polymer with hydration sites, polyvinylalcohol with a molecular weight of 20,000 (Mowiol 4-98, Hoechst) is added to be present as 22% of the final product. Polyvinylpyrrolidone of molecular weight 40,000 is added to be present in an amount of 4.0 percent. Water is added in an amount to yield a total final composition weight of 38 percent (deionized water is used in the experiments). After each of the mentioned components has been added to the vessel, which typically may be a beaker for experimental studies, the components are thoroughly mixed. The resultant mixture is placed in a microwave oven and heated to the boiling point. The beaker is then covered and thereafter transferred to a steam bath and the process continued until full extension of the polymers contained in the mixture occurs.

A trinitroglycerol solution prepared in accordance with Example IV is added to the above mixture followed by stirring and mixing well. The resultant liquid matrix is then cast between two sheets of a foil laminate, allowed to set, yielding the desired polymeric matrix now suitable for use as a transdermal system for the sustained release of trinitroglycerol.

The matrix is not as suitable as the preferred embodiment, since it is too wet, although strong.

EXAMPLES LI–XCIV (44 examples)

Substituting the triturate of Example I for the trinitroglycerol solutions of Examples IX–LII, polymeric diffusion matricies free from disaccharides are produced that may be used as a polymeric diffusion matrix in accordance with the first aspect of the invention.

EXAMPLE XCV

"Stock Solution A" is prepared by mixing together polyvinylpyrrolidone (mw 40,000), isopropanol, and isopropyl myristate. Sodium borate is added to this mixture to complete the preparation of Stock Solution A.

"Stock Solution B" is made up of 88% hydrolyzed polyvinylalcohol (mw 10,000) having 10% nitroglycerin by weight bound thereto as a triturate, to which is added water and isopropyl alcohol.

The total weight of the ingredients of the combined solutions above provide the following, the isopropyl alcohol being split between the two stock solutions:

| | |
|---|---|
| Polyvinylpyrrolidone | 24.9% |
| Polyvinylalcohol | 17.2% |
| Isopropyl myristate | 4.8% |
| Isopropyl alcohol | 28.7% |
| Water | 17.2% |
| Sodium borate | 2.3% |
| Trinitroglycerol | 2.0% |

In splitting the isopropyl alcohol between the two stock solutions, 75% is advantageously put into the polyvinylpyrrolidone "A" and the remainder in the polyvinylalcohol "B" stock solutions, respectively.

After each stock solution is prepared, the two are mixed together to provide a fixed dimension gel which is cast in accordance with Example VI and a bandage produced in accordance with the aforementioned Keith et al. patent.

EXAMPLE XCVI

In addition to the substantially-disaccharide free polymeric diffusion matrix of the invention, flowable gels, buccal, and sublingual forms are also produced with the triturates of Examples I–IV. The following examples illustrate these aspects of the invention:

EXAMPLE XCVII

The triturate of Example II is mixed with water to form a 5% polymer concentration, and shows a limited amount of phase separation.

EXAMPLE XCVIII

The product of Example II is incorporated into a matrix system similar to that of the above-mentioned Keith et al. patent. An aqueous solution of 17% fully extended polyvinylalcohol having a molecular weight of 115,000 and 5% polyethylene glycol (mw 1000) is heated to a temperature of about 90° C. After thorough mixing, cooling to 50° C. is permitted, and the product of Example II is added. After a homogeneous mixture is obtained, the resultant mixture is cast onto a sheet to form a fixed dimension gel which can be used in place of the sustained release diffusion matrix of Example I of the Keith et al. patent.

EXAMPLE XCIV

A buccal form is provided by the production of a fixed dimension gel in accordance with the general procedures of Example VIII, but without isopropyl alcohol and isopropyl myristate. A laminate structure is made with a backing; an adhesive is placed on the other face to provide a buccal form that can be placed in the cheek of a patient.

EXAMPLE C

A sustained release oral tablet is provided by compressing the following ingredients together, the amounts given being in weight per tablet:

| | |
|---|---|
| 100 mg | powder of Example I (containing 10% trinitroglycerol) |
| 50 mg | glycerol monostearate |
| 30 mg | methyl cellulose |
| 50 mg | ethyl cellulose |
| 30 mg | fat wax |
| 40 mg | magnesium stearate |

The resultant tablet is taken by the patient under the tongue, resulting in a relatively rapid release of the trinitroglycerol to the patient.

EXAMPLE CI

A sublingual tablet is provided by compressing together the following ingredients, the amounts being given in weight per tablet:

| | |
|---|---|
| 4 mg | Powder of Example I |
| 50 mg | powdered cellulose |
| 3 mg | magnesium stearate |
| 2 mg | glyceryl monostearate |

The tablet thus produced may be taken by the patient under the tongue as in Example IX, resulting in a rapid initial release of nitroglycerin to the patient.

EXAMPLE CII

In the process of Example VI, instead of using the triturate of Example II, trinitroglycerol is directly introduced into the manufacturing process in a suitable solvent, e.g., acetone, an equimolar amount of trinitroglycerol in such solvent being added in place of the product of Example II. It should be noted that this embodiment is extremely dangerous due to the explosive characteristic of trinitroglycerol, and should only be carried out in areas safeguarded from explosions, such as at dynamite factories.

What is claimed is:

1. A polymeric diffusion matrix for the transdermal systemic delivery of polymeric fixed dimension gelled trinitroglycerol through the skin of a patient comprising about 10 to about 40% of
   a first lower molecular weight polyvinylalcohol component that is hydrolyzed to a degree of hydrolysis of about 75 to about 92% and has a molecular weight in the range of from about 5,000 to about 40,000; about 2% to about 15% of
   a second higher molecular weight polyvinylalcohol component that is hydrolyzed to a degree of hydrolysis of at least 95% and has a molecular weight in the range of from about 90,000 to about 150,000; and about 2 to about 25% of
   glycerol, said polymeric diffusion matrix containing sufficient substantially disaccharide-free trinitroglycerol bound to a polymer as a triturate in a non-explosive flowable fixed dimension gel form, said polymer being selected from the group consisting of polyvinyl alcohol, polyvinylpyrrolidone, polyvinyl acetate, polyethylene glycol, polymethacrylate, polymethyl methacrylate, ethyl acrylate-vinyl chloride polymer, and mixtures thereof to be released over a prolonged period of time.

2. The polymeric diffusion matrix of claim 1 further comprising up to about two percent by weight of polyvinylpyrrolidone having a molecular weight of from about 20,000 to about 60,000.

3. The polymeric diffusion matrix of claim 1 further comprising an alkanolamide present in an amount of up to about 5% by weight.

4. The polymeric diffusion matrix of claim 3, wherein said alkanolamide is present in an amount of from about 0.1 to about 3% by weight.

5. The polymeric diffusion matrix of claim 1, 3, 2, 3, or 4, further comprising a backing layer adhered to one surface of said polymeric diffusion matrix, said backing layer having a larger surface area than said polymeric diffusion matrix, and an adhesive layer attached to said backing layer on the same side thereof as said polymeric diffusion matrix, whereby said polymeric diffusion matrix is maintained in diffusional contact with the skin of said patient.

6. The polymeric diffusion matrix of claim 1, 3, 2, 3, or 4, further comprising a facestock layer with skin adhesive which permits the self-adhesion of said polymeric matrix to the skin of said patient.

7. The polymeric diffusion matrix of claim 1, wherein said first lower molecular weight component is hydrolyzed to a degree of hydrolysis of about 86 to 90%.

8. The polymeric diffusion matrix of claim 7, wherein said second higher molecular weight component has a degree of hydrolysis of about 98 to 99%.

* * * * *